United States Patent [19]

Drury

[11] 4,026,712
[45] May 31, 1977

[54] MICROORGANISM INHIBITORS

[75] Inventor: Emma-Jane E. Drury, Rochester, N.Y.

[73] Assignee: Eastman Kodak Company, Rochester, N.Y.

[22] Filed: Mar. 29, 1976

[21] Appl. No.: 671,211

Related U.S. Application Data

[63] Continuation-in-part of Ser. No. 508,312, Sept. 25, 1974, abandoned.

[52] U.S. Cl. .............................. 106/15 R; 106/16; 424/317
[51] Int. Cl.² .............................................. C09D 5/14
[58] Field of Search ............... 106/15 AF, 15 R, 16, 106/17, 18; 260/514 G; 424/317

[56] References Cited
UNITED STATES PATENTS 2,688,021  8/1954  Jenkins .................... 260/514 G
3,796,803  3/1974  Strong ...................... 424/316

OTHER PUBLICATIONS

Chemical Abstracts, vol. 66, 1967, p. 1839, No. 18904v.
Chemical Abstracts, vol. 75, 1971, p. 223, No. 128978r.

Primary Examiner—Paul R. Michl
Attorney, Agent, or Firm—John F. Stevens; Daniel B. Reece III

[57] ABSTRACT

Norbornane-2 and norbornene-2-carboxylic acid compounds of the formula

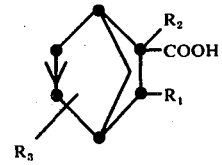

wherein Y is a single or double bond, $R_1$, $R_2$ and $R_3$ are each hydrogen or alkyl groups having from 1 to 8 carbon atoms are used as microorganism inhibitors in aqueous suspensions or emulsions.

22 Claims, No Drawings

MICROORGANISM INHIBITORS

This is a continuation-in-part of United States application Ser. No. 508,312 filed Sept. 25, 1974, now abandoned.

This invention relates in general to use of norbornane and norbornene derivatives to inhibit the growth of microorganisms, and more particularly this invention relates to the use of norbornane-2 and norbornene-2-carboxylic acids as microorganism inhibitors in aqueous suspensions or emulsions.

Bacterial activity in such emulsions as paint is undersirable because it drastically reduces or destroys cellulosic thickeners, which are often used in aqueous paint emulsions, by producing a chemical catalyst, the cellulase enzyme. Such microorganism growth has various other detrimental effects in other aqueous emulsions. Microbiocides are widely used in aqueous emulsions, such as aqueous latex paint emulsions. Since microorganisms grow readily in many aqueous emulsions, a bactericide is required to prevent microbial growth in the containers. In the past, phenylmercuric acetate has been widely used as an "in-can" microbiocide.

The use of mercury-containing compounds in some emulsions has recently been banned by the Environmental Protection Agency. Aqueous emulsions must be reformulated to incorporate non-mercurial biocides with high activity. There are some non-mercurial biocides on the market already, none of which are completely effective at manufacturers recommended use levels.

The norbornane and norbornene derivatives of this invention may be used as microorganism inhibitors in aqueous suspensions and emulsions such as fiber lubricants, warp size emulsions, floor polishes and waxes, wax emulsions for fruit coatings, inks, aqueous suspensions of wood pulp, leather treatment systems, polyester based enamels, and water treatment systems, in addition to the aqueous paint emulsions.

It is therefore an object of this invention to provide an effective microorganism inhibitor for aqueous suspensions or emulsions.

It is another object of this invention to provide a method of inhibiting the growth of microorganisms in aqueous paint emulsions to thereby retain the proper thickness and viscosity.

Other objects and advantages of the present invention will appear herein.

According to this invention, certain norbornane-2 and norbornene-2-carboxylic acids are blended into aqueous emulsions to inhibit the growth of microorganisms. Such acids are broadly described as those having the general formula

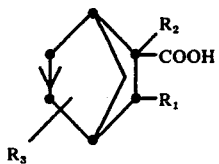

wherein Y is a single or double bond, $R_1$, $R_2$ and $R_3$ are each hydrogen or a lower alkyl group. By the term "lower alkyl" it is meant alkyl having from 1 to 8 carbon atoms.

The norbornane-2 and norbornene-2-carboxylic acids described above are prepared by reacting cyclopentadiene, or lower alkyl derivatives thereof with $\alpha,\beta$-unsaturated carboxylic acids of from 3 to 19 carbon atoms. The carboxylic acids may be either straight or branched chain and include such acids as acrylic, methacrylic, and crotonic, which are preferred. It is preferred to use cyclopentadiene as a reactant. Cyclopentadiene and dicyclopentadiene normally occur in equilibrium mixtures at room temperatures, but upon heating, the monomer is obtained in greater amounts.

Especially preferred norbornane or norbornene-2-carboxylic acids include 3-methyl-5-norbornene-2-carboxylic acid, 5-norbornene-2-carboxylic acid and norbornane-2-carboxylic acid.

Examples I, II and III are submitted to illustrate preparation of the norbornane-2 and norbornene-2-carboxylic acids.

EXAMPLE I

The $\alpha,\beta$-unsaturated acid (1.0 mole) and dicyclopentadiene (0.55 mole) are heated at 160°–180° C for 3–8 hours under atmospheric or superatmospheric pressure, depending on the boiling point of the acid. The mixtures are separated by fractional distillation to afford the norbornene-carboxylic acids (0.50–0.90 mole).

EXAMPLE II

Dicyclopentadiene is distilled at atmospheric pressure to yield cyclopentadiene monomer, b.p. 38°–40° C., which is used as soon as possible. The monomer (1.0 mole) is added to methacrylic acid (1.0 mole) at 40°–45° C. An exothermic reaction results, with refluxing of cyclopentadiene as the temperature of the mixture rises slowly to 85° C. Fractional distillation affords, after a forerun of dicyclopentadiene and unreacted methacrylic acid, 2-methyl-5-norbornene-2-carboxylic acid (0.65 mole), b.p. 103°–106° C. at 1.5 torr. There is virtually no high boiling residue. This method is particularly useful for acids which polymerize readily at higher temperatures.

EXAMPLE III

A solution of 5-norbornene-2-carboxylic acid (0.25 mole) in 100 ml. of ethyl acetate is hydrogenated over 5% palladium on carbon catalyst at 40 psi and 30°–50° C. The theoretical amount of hydrogen is absorbed exothermically within 0.5 hour. Removal of catalyst and solvent affords a residue of essentially pure norbornane-2-carboxylic acid, as indicated by infrared, NMR, and glpc analyses. The substituted acids are reduced readily in the same way.

The norbornane-2 and norbornene-2-carboxylic acids used in accordance with this invention are mixed with aqueous emulsions in an amount of from about 0.12 to about 0.95 parts acid per 100 parts by weight of the suspension or emulsion. In other words, the acid is used at a level of from about 0.1 to 0.08 pound per gallon of aqueous suspension or emulsion. In aqueous latex paint emulsions, the weight of the paint is about 10 pounds per gallon. A typical aqueous latex paint may have the following composition:

|  | Gallons |
|---|---|
| Hydroxyethyl cellulose (2.5% solution) | 10.30 |
| Emulsifiers | 1.40 |
| Latex | 44.39 |
| Coalescents | 5.19 |
| Driers | 3.69 |

| | Gallons |
|---|---|
| Additives, e.g., pigments, stabilizers | 19.60 |
| Water | 15.43 |
| | 100.00 |

The norbornane-2 or norbornene-2-carboxylic acids may be mixed with the emulsion by methods well known in the art, such as by blending and stirring until a good mixture has been attained.

The most widely used microbiological methods available for testing the activity of biocides as in-can preservatives for aqueous paint emulsions are inhibition zone tests (agar plates), dilution tube tests (bacterial inhibition in nutrient broth) and the effectiveness of a biocide in protecting finished paint formulations against multiple inoculation (multiple insult test). Of these three, the multiple insult test represents the most reliable method for the evaluation of a microbiocide under conditions of practical utility.

The procedure used for the multiple insult test is as follows:

Preparation of Contaminated Paint

The paint to be tested is inoculated with a 2-day old mixed culture of organisms, either wild strains from contaminated paint or a mixture of cultures of bacteria such as *Pseudomonas aeruginosa*, *Aerobacter aerogenes* and *Proteus vulgaris*, at a level of 10 ml. culture per gallon of paint. The paint thus inoculated is stirred and/or shaken to mix well and incubated at 37° C. for 4 days. One ml. of the incubated, inoculated paint is diluted with 99 ml. sterile distilled water and 0.1 ml. of this is streaked on nutrient agar. The agar plates are incubated at 37° C. for 4 days at which time the number of colonies present is counted. If the colonies are too dense to count accurately, further dilution may be necessary. Ideally the contaminated paint should contain approximately $2 \times 10^5$ to $2 \times 10^6$ organisms per ml. of paint to limit the number of necessary dilutions for easy counting.

Addition of Biocide

Five 100 ml. portions of contaminated paint are measured into 8 oz. glass screw-cap bottles. The biocide to be tested is added at levels of 0, 1, 2, 4 and 8 lbs./100 gallons of paint. Number of levels and the levels chosen are arbitrary and are varied to accommodate a specific biocide. A range of biocide levels is necessary in order to determine the minimum amount necessary for protection. If in the initial test, the results do not range from complete contamination, through medium contamination to zero contamination, the biocide is tested with addition levels increased or decreased in order to obtain this range. However, levels higher than 8 pounds per 100 gallons of paint are not economically attractive.

Samples are mixed by stirring, loosely capped and incubated 24 hours at 37° C. One ml. portions of each incubated sample are diluted and streaked on nutrient agar to determine antimicrobial activity of a preservative.

Multiple Insult Test

On the first day, the test samples (contaminated paint with added biocide) are challenged (insulted) with 1 ml. of control paint containing no biocide incubated 24 hours at 37° C. On the second day, each sample is aseptically streaked on nutrient agar. The paint samples are again insulted with 1 ml. of the control. All samples and petri plates are incubated at 37° C. On the third day, after 24 hours incubation, the petri plates are examined for contamination. The final examination of the petri plates is made after incubation for 96 hours. The 24 hour examination yields an early indication of the degree of contamination remaining in the test samples. If contamination is great, the sample is not reinsulted and is discarded. The remainder of the test consists of repeating the multiple insult test 9 more times. Samples that maintained sterility are insulted and plated every 24 hours. In order to complete the test successfully, a preserved sample should remain sterile through 10 insults while the control is heavily contaminated.

Selected norbornene-2 and norbornane-2-carboxylic acids are tested in an inexpensive commercial brand of latex paint of the general formula given hereinbefore. In order to assure adequate contamination of the paint, it is inoculated with a mixture of cultures of the bacteria *Psuedomonas aeruginosa*, *Aerobacter aerogenes* and *Proteus vulgaris* at a level of 10 ml. cultures/gallon of paint. Test compounds are evaluated at levels of 1, 2, 4 and 8 lbs./100 gallons paint (ca. 0.12%, 0.24%, 0.48% and 0.95% respectively). A sample of the contaminated paint is evaluated in the same manner as the test compounds as a control. The "multiple insult" test is the method used to evaluate the microbiocidal activity of the norbornene-2 and norbornane-2-carboxylic acids.

The above-identified compounds are tested by recording the insult number at "failure". Failure is defined as any amount of bacterial growth on the agar plate.

EXAMPLE IV

Norbornene-2-carboxylic acid of the formula

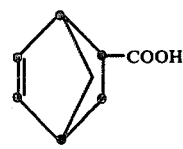

is tested by blending it with an aqueous latex paint emulsion at the rate of 1 lb. per 100 gallons of paint. The pH of the acid is 4.0 and it has a solubility of 8 lbs. per 100 gallons of paint. Failure is noted at an insult number of 4.

EXAMPLE V

Norbornane-2-carboxylic acid of the formula

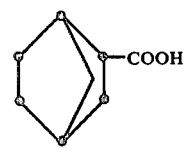

is tested by blending it with an aqueous latex paint emulsion at the rate of 1 lb. per 100 gallons of paint. The pH of the acid is 3.5 and it has a solubility of 8 lbs. per 100 gallons of paint. Failure is noted at an insult number of 2.

EXAMPLE VI

Norbornane 2-carboxylic acid of the formula

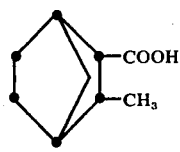

is tested by blending it with an aqueous latex paint emulsion at the rate of 2 lbs. per 100 gallons of paint. The pH of the acid is 5.0 and it has a solubility of 2 lbs. per 100 gallons of paint. Failure is noted at an insult number of 9.

EXAMPLE VII

Norbornene 2-carboxylic acid of the formula

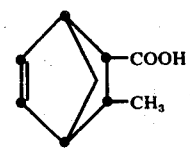

is tested by blending it with an aqueous latex paint emulsion at the rate of 2 lbs. per 100 gallons of paint. The pH of the acid is 4.5 and it has a solubility of 2 lbs. per 100 gallons of paint. Failure is noted at an insult number of 9.

High solubility and low pH appear to have a direct relationship to the observed activity of the compounds. The most active compounds were, in general, on the acid side and were more soluble in water. Latex paints contain a certain amount of emulsifiers which will enhance the solubility. However, when testing the insoluble compounds, notably the amines, bits of solid material from the derivatives were detectable in the paint. Use of additives or complexes to increase the solubility might increase the effective biocidal activity of the norbornene and norbornane amines.

In the above examples, pH determination is by using a 45.5:50:0.5 ratio of isopropanol:benzene:water as a solvent. 0.1 ml. of the acid is dissolved in 10 ml. solvent. Panpeha brand pH paper is used for pH determination. Solubility is determined by adding the acid to water and stirring vigorously. The presence of oil drops in the bottom of the container or oily film on the surface of the water is noted.

Unless otherwise stated, all parts, percentages, ratios, etc. are by weight.

The following examples are illustrations of the use of norbornane and norbornene carboxylic acid compounds as microorganism inhibitors in other aqueous suspensions or emulsions. In each instance the suspension or emulsion is subjected to the Multiple Insult Test described above. The samples containing the norbornane, norbornene-carboxylic acid compounds successfully passed the test.

EXAMPLE VIII

Aqueous Suspensions of Wood Pulp

The mechanical pulping of wood consists of grinding and soaking wood chips in water. Microorganisms proliferate in the water. A biocide to eliminate these organisms to prevent build-up of slime, algae, and bacteria is needed. A norbornane compound is added as a biocide to water used for the grinding and soaking of wood pulp. An example of such a formulation is as follows:

| | |
|---|---|
| Wood chips | 20.00 lbs. |
| Norbornane-2-carboxylic acid | 0.24 lbs. |
| Water | 79.76 lbs. |
| | 100.00 lbs. |

EXAMPLE IX

When wood pulp is processed chemically, the resultant fiber must be washed with water to free it of added chemicals. This water is an excellent medium for the growth of microorganisms because of gradual accumulation of cellulosic matter. Other steps in the pulping process such as bleaching, knotting and screening also involve water slurries. The water in all these processes may contain molds, bacteria, and algae.

A norbornene compound is added as a biocide to these wash waters or washing slurries to prevent microbial build-up. An example is the addition of 2 lbs. of 5-norbornene-2-carboxylic acid to every 100 gallons of wash water or slurry.

EXAMPLE X

Fiber Lubricants

Fiber lubricants are used both in the spinning of yarns and in the knitting of yarns. These lubricants because of their composition are subject to microbial degradation during use when they are stored in open containers or left in lines. Bactericides now currently used are formaldehyde and orthophenylphenol. These biocides have relatively high mammalian toxicity.

This example relates to the addition to a fiber lubricant of norbornene-norbornane compounds as biocides with low mammalian toxicity.

Such formulations include:

| | |
|---|---|
| Light mineral oil | 90.00 lbs. |
| Norbornane-2-carboxylic acid | 0.24 lbs. |
| Nonionic emulsifying agent | 9.76 lbs. |
| | 100.00 lbs. | or

| | |
|---|---|
| Carrier containing for example: Butyl stearate esters, polyethylene glycol monostearate and mineral oil | 85.00 lbs. |
| Antistat | 1.00 lbs. |
| Friction modifier | 0.50 lbs. |
| Synthetic wax | 1.76 lbs. |
| Emulsifying agent | 10.00 lbs. |
| Blending agent | 0.50 lbs. |
| Lactic acid (pH adjuster) | 1.00 lbs. |
| 5-Norbornene-2-carboxylic acid | 0.24 lbs. |
| | 100.00 lbs. |

EXAMPLE XI

Floor Polishes and Waxes

The use of emulsified waxes and polishes for home and industrial use is popular because of their ease of handling and their highly buffable, detergent-resistant properties. These aqueous emulsions can be subject to in-can microbial attack. Emulsified waxes and polishes which are not frequently buffed or "stripped" before applying a new wax surface can show microbial degradation in certain climates.

A norbornene compound is added as a biocide to wax emulsions for the purpose of preventing the growth of microorganisms both in-can and on waxes surfaces. Such a formulation is as follows:

| | |
|---|---|
| Emulsion based on natural and synthetic waxes | 13.200 lbs. |
| Resin solution | 1.500 lbs. |
| Tributoxyethyl phosphate | 0.980 lbs. |
| Ethylene glycol | 0.980 lbs. |
| Surfactant | 0.005 lbs. |
| 5-Norbornene-2-carboxylic acid | 0.240 lbs. |
| Water | 83.095 lbs. |
| | 100.000 lbs. |

EXAMPLE XII

Hides and Leather Treatment

An established method for preserving green (fresh) cattle hides from the time they fall from the animal until they reach the tanneries is called "brinning". This procedure involves immersing the hides in a aqueous saturated sodium chloride solution containing a bactericide such as sodium hypochlorite or sodium silicofluoride. The discharge, after use, of these solutions into existing sewers or streams will be severely restricted in 1983 by EPA.

Prior to tanning, salted hides are "soaked" (rehydrated). Bactericides used in this soak are chlorinated phenols, beta-naphthol, mercurials, and para-chloro-meta-cresol. These bactericides either have been banned recently or may be banned soon due to potential environmental contamination.

A norbornane compound is added as a bactericide to "brinning" and soaking solutions to prevent the discharge of environmentally undesirable materials into streams and sewers.

For a brinning solution with a hide to water weight of one to five, add 2 lbs. of 5-norbornene-2-carboxylic acid to 100 gallons water.

For a soak solution with a hide to water weight of one to five use:

| | |
|---|---|
| Sodium chloride | 10.00 lbs. |
| Sodium sulfate | 1.00 lbs. |
| Norbornane-2-carboxylic acid | 0.24 lbs. |
| Water | 88.76 lbs. |
| | 100.00 lbs. |

EXAMPLE XIII

Polyester-Based Enamels

Enamel formulations based on fast drying solvents have been used for more than 30 years in the coating industry. Now, with concerns such as environmental and energy conservation, the paint industry is turning from expensive petroleum-based raw materials to aqueous emulsions. Water-based latex paints have been successfully used for years; recently, aqueous polyester-based enamels were introduced. In the past, mercurials have been used as biocides in water-based paints; these biocides were recently banned by EPA.

A norbornane compound is added as a biocide in polyester-based paint. An example of such a formulation is:

| | |
|---|---|
| Pigment | 22.50 lbs. |
| Polyester water-reducible resin | 25.64 lbs. |

-continued

| | |
|---|---|
| Cymel 303 resin | 5.23 lbs. |
| Dimethylethanolamine | 1.90 lbs. |
| Catalyst | 0.27 lbs. |
| Organic solvent | 3.00 lbs. |
| Flow control in 10% butanol | 0.27 lbs. |
| Norbornane-2-carboxylic acid | 0.24 lbs. |
| Water | 40.95 lbs. |
| | 100.00 lbs. |

EXAMPLE XIV

Warp Size Emulsions

Spun or polyester filament yarns have found widespread use in a variety of fabrics. Sizing, either starch or synthetic polymers, is used to encapsulate yarns to prevent breakage, fuzz-ball formations, shedding or build-up, and tangling so they may withstand the abrasive and tensile forces of weaving. Yarn and the sizing emulsion are placed in "kettles" where the sizing emulsion will penetrate the yarn. These kettles of aqueous emulsion contain materials, such as starch, which will enhance the growth of microorganisms.

Norbornane and norbornene compounds are added as biocides to sizing emulsions to prevent microbial growth. An emulsion for a polyester blend is as follows:

| | |
|---|---|
| Thin boiling starch | 45.00 lbs. |
| Polyvinyl alcohol | 45.00 lbs. |
| Natural wax | 9.76 lbs. |
| 5-Norbornene-2-carboxylic acid | 0.24 lbs. |
| | 100.00 lbs. |
| A sizing emulsion for rayon or cotton is: | |
| Douglas pearl starch X | 10.19 lbs. |
| Wax | .48 lbs. |
| Norbornane-2-carboxylic acid | .24 lbs. |
| Water | 89.09 lbs. |
| | 100.00 lbs. |

EXAMPLE XV

Water Based Inks

Inks are used on a wide variety of papers and paperboards. Water-based flexographic inks usually contain vehicles based on alkali-soluble proteins such as casein or zein. The presence of protein provides an excellent medium in which bacteria and/or mold can develop rapidly. If the ink is allowed to stand in open containers or in lines not in continuous use or applied to cartons that do not permit rapid drying, microbial degradation of the ink will occur.

A norbornene compound is added as a biocide to water-based inks in order to prevent microbial degradation of the ink. A formulation is as follows:

| | |
|---|---|
| Barium lithol red | 15.00 lbs. |
| Microcrystalline wax | 1.00 lbs. |
| Alpha protein | 5.00 lbs. |
| Esterified fumarated rosin | 10.00 lbs. |
| 26° Be Ammonium hydroxide (29.1% NH$_3$ by wt.) | 2.00 lbs. |
| Octyl alcohol | 5.00 lbs. |
| 5-Norbornene-2-carboxylic acid | 0.24 lbs. |
| Water | 61.76 lbs. |
| | 100.00 lbs. |

EXAMPLE XVI

Water Treatment System

Circulating water systems, such as those used for air cooling, are treated with biocides to control bacteria, mold/slimes and algae. Small systems, 5000 to 6000 gallons, use sodium silicofluoride as a biocide. Larger systems, over 10,000 gallons, are generally treated with chromate salts or sodium pentachlorophenol. These biocides are potential environmental contaminants because of their toxicity to mammals.

This invention relates to the addition of a biocide with low mammalian toxicity to circulating water systems. An example of this biocidal treatment consists of adding 2 lbs. of 5-norbornene-2-carboxylic acid to each 100 gallons of circulating water.

EXAMPLE XVII

Wax Fruit and Vegetable Coatings

A number of resins and waxes, both natural and synthetic, are used as coatings for fruits and vegetables. Their purpose is: (1) to maintain or enhance the natural gloss, feel, and taste of the product for a longer time period; and (2) prevent the loss of moisture and shrinkage. Fresh produce is subject to microbial deterioration. The addition of a biocide to the wax coating on fresh produce would enhance their storage life.

A norbornane compound is added as a biocide to an emulsifiable wax coating for fresh produce to enhance storage life. A formulation is as follows:

| | |
|---|---|
| Emulsifiable synthetic wax | 14.18 lbs. |
| Paraffin 130–140° AMP | 4.72 lbs. |
| Oleic acid | 3.31 lbs. |
| Morpholine | 2.84 lbs. |
| Norbornane-2-carboxylic acid | 0.24 lbs. |
| Water | 74.71 lbs. |
| | 100.00 lbs. |

Although the invention has been described in considerable detail with particular reference to certain preferred embodiments thereof, variations and modifications can be effected within the spirit and scope of the invention.

I claim:

1. An aqueous suspension of a substance normally susceptable to the growth of microorganisms having contained therein a microorganism inhibiting quantity of a compound of the formula

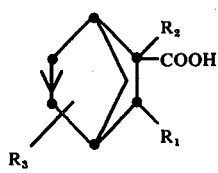

wherein Y is a single or double bond, and $R_1$, $R_2$ and $R_3$ are each hydrogen or lower alkyl.

2. An aqueous suspension according to claim 1 wherein said compound is present in an amount of from about 0.12 to about 0.95 parts by weight per hundred parts of said aqueous suspension.

3. An aqueous suspension according to claim 1 wherein $R_1$ and $R_2$ of said compound are both hydrogen.

4. An aqueous suspension according to claim 1 wherein $R_1$ of said compound is hydrogen and $R_2$ of said compound is methyl.

5. An aqueous suspension according to claim 1 wherein $R_1$ of said compound is methyl and $R_2$ of said compound is hydrogen.

6. An aqueous suspension according to claim 1 wherein said suspension is selected from the group consisting of an aqueous suspension of wood pulp, a brinning solution or a soaking solution for hides and leather treatment, and a water based ink.

7. An aqueous emulsion of a substance normally susceptable to the growth of microorganisms having contained therein a microorganism inhibiting quantity of a compound of the formula

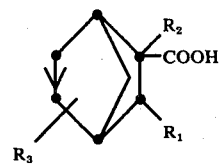

wherein Y is a single or double bond, and $R_1$, $R_2$ and $R_3$ are each hydrogen or lower alkyl.

8. An aqueous emulsion according to claim 7 wherein said compound is present in an amount of from about 0.12 to about 0.95 parts by weight per hundred parts of said aqueous emulsion.

9. An aqueous emulsion according to claim 7 wherein $R_1$ and $R_2$ of said compound are both hydrogen.

10. An aqueous emulsion according to claim 7 wherein $R_1$ of said compound is hydrogen and $R_2$ of said compound is methyl.

11. An aqueous emulsion according to claim 7 wherein $R_1$ of said compound is methyl and $R_2$ of said compound is hydrogen.

12. An aqueous emulsion according to claim 7 wherein the emulsion is selected from the group consisting of fiber lubricants, floor polishes and waxes, polyester-based enamels, warp size emulsion, and wax fruit and vegetable coatings.

13. An aqueous latex paint emulsion having contained therein a microorganism inhibiting quantity of a compound of the formula

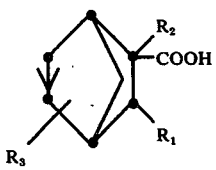

wherein Y is a single or double bond, and $R_1$, $R_2$ and $R_3$ are each hydrogen or lower alkyl.

14. An aqueous latex paint emulsion according to claim 13 wherein said compound is present in an amount of from about 0.12 to about 0.95 parts by weight per hundred parts of said aqueous latex paint emulsion.

15. The method of inhibiting the growth of microorganisms in aqueous suspensions of a substance normally susceptable to the growth of microorganisms which comprises adding to said aqueous suspension an inhibiting quantity of a compound of the formula

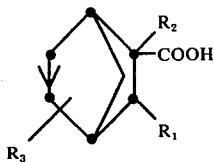

wherein Y is a single or double bond, and $R_1$, $R_2$ and $R_3$ are each hydrogen or lower alkyl.

16. The method according to claim 15 which comprises adding from about 0.12 to about 0.95 parts of said compound per hundred parts of said aqueous suspension.

17. The method according to claim 18 wherein the aqueous suspension is selected from the group consisting of an aqueous suspension of wood pulp, a brinning solution or a soaking solution for hides and leather treatment, and a water based ink.

18. The method of inhibiting the growth of microorganisms in aqueous emulsions of a substance normally susceptable to the growth of microorganisms which comprises adding to said aqueous emulsions an inhibiting quantity of a compound of the formula

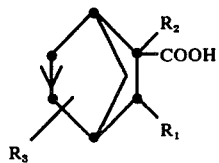

wherein Y is a single or double bond, and $R_1$, $R_2$ and $R_3$ are each hydrogen or lower alkyl.

19. The method according to claim 18 which comprises adding from about 0.12 to about 0.95 parts of said compound per hundred parts of said aqueous emulsion.

20. The method according to claim 18 wherein the emulsion is selected from the group consisting of fiber lubricants, floor polishes and waxes, polyester-based enamels, warp size emulsions, and wax fruit and vegetable coatings.

21. The method of inhibiting the growth of microorganisms in aqueous latex paint emulsions which comprises adding to said paint emulsions an inhibiting quantity of a compound of the formula

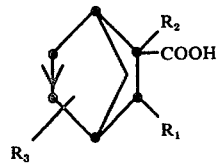

wherein Y is a single or double bond, and $R_1$, $R_2$ and $R_3$ are each hydrogen or lower alkyl.

22. The method according to claim 21 which comprises adding from about 0.12 to about 0.95 parts of said compound per hundred parts of said aqueous latex paint emulsion.

* * * * *

UNITED STATES PATENT OFFICE
CERTIFICATE OF CORRECTION

Patent No. 4,026,712          Dated May 31, 1977

Inventor(s) Emma-Jane E. Drury

It is certified that error appears in the above-identified patent and that said Letters Patent are hereby corrected as shown below:

Column 11, line 16, after claim, delete "18" and insert ---15---.

Signed and Sealed this twenty-third Day of August 1977

[SEAL]

Attest:

RUTH C. MASON
Attesting Officer

C. MARSHALL DANN
Commissioner of Patents and Trademarks